United States Patent [19]
Kubalak et al.

[11] Patent Number: 5,454,798
[45] Date of Patent: Oct. 3, 1995

[54] DISPOSABLE URINE BAG

[75] Inventors: Thomas P. Kubalak, Plymouth; Daniel P. Welch, Zimmerman, both of Minn.; Daniel J. Habecker, Santa Barbara, Calif.

[73] Assignee: Mentor Corporation, Minneapolis, Minn.

[21] Appl. No.: 61,901

[22] Filed: May 14, 1993

[51] Int. Cl.$^6$ ..................................................... A61F 5/44
[52] U.S. Cl. ..................... 604/328; 604/349; 604/326; 128/761
[58] Field of Search ..................................... 128/761, 768; 604/326–331, 346–353, 4/144.1–144.4

[56] References Cited

U.S. PATENT DOCUMENTS

| | | | |
|---|---|---|---|
| 4,204,527 | 5/1980 | Wu et al. | 604/349 |
| 4,230,115 | 10/1980 | Walz et al. | 604/349 |
| 5,147,341 | 9/1992 | Starke et al. | 604/349 |

Primary Examiner—Randall L. Green
Assistant Examiner—Rob Clarke
Attorney, Agent, or Firm—Hugh D. Jaeger

[57] ABSTRACT

A disposable urine bag having sealed cavity members where one cavity stores an extendable catheter and also acts as a urine storage reservoir. A second sealed and peel-away cavity includes a catheter advancement mechanism which provides for lubricated catheter advancement without actual contact of the catheter by the human hand. An absorption member is provided to semi-solidify urine stored in the urine storage reservoir.

31 Claims, 6 Drawing Sheets

5,454,798

DISPOSABLE URINE BAG

CROSS REFERENCES TO CO-PENDING APPLICATIONS

This patent application relates to U.S. patent application Ser. No. 07/989,517, filed Dec. 11, 1992, entitled "Disposable Urine Bag", and to the same assignee as the present patent application.

BACKGROUND OF THE INVENTION

1. Field of the Invention

The present invention pertains to a bodily waste collector bag, and more particularly, pertains to a disposable urine bag and a process for extending an extendable catheter disposed from the interior of the urine bag.

2. Description of the Prior Art

Prior art urine bags have a multiplicity of members constructed in a fashion where the catheter is an external device which must be attached to the urine bag. Other prior art urine bags have required a great deal of dexterity to manipulate the catheter from out of the bag. Accidental touching of the catheter could result in contamination of the sterile surface of the catheter. Subsequent to urine disposition within the bag, the urine bag required sealing by a cap or other device to contain the urine within the urine bag. Disposing of some of the prior art urine bags created a problem in that a bag and a catheter, as separate units, had to be disposed of carefully. Prior art urine bags could also be accidentally punctured prior to disposal, thus creating an undesirable fluid leakage around and about the urine bag and the person.

The present invention overcomes the problems of the prior art urine bag devices by providing a single unit, disposable urine bag having a self-contained, extendable catheter and having a urine absorbing chemical or mechanism within the urine bag.

SUMMARY OF THE INVENTION

The general purpose of the present invention is to provide a single unit disposable urine bag having a self-contained and stored extendable catheter with an advancement mechanism, which is a part of the urine bag. A highly absorbent chemical stored in the urine bag cavity reacts with urine to produce a semi-solid like mass within the confines of the urine bag, thus alleviating spillage of urine from the urine bag. Alternatively, a drain is incorporated to drain urine from the interior of the urine bag cavity, such as for testing of the urine or disposal of the urine.

According to one embodiment of the present invention, there is provided a flexible disposable urine bag having one or more cavities formed between joined flexible top and bottom plastic members. Formable and sealable pockets or cavities are formed by electronic, RF, ultrasonic, induction, thermal adhesive or other suitable welds between the flexible top and bottom flexible polymer members. An advancement mechanism is secured within one sealed and detachable cavity of the collection device with its majority structure extending from the sealed edge of a sealed reservoir or cavity area containing an advanceable catheter. The advancement mechanism can also lubricate and slidably seals the catheter to prevent leakage of urine from the sealed cavity reservoir, and also allows for easy passage of the catheter out of the reservoir without contact with human hands. The stored catheter, having a conical-shaped rubber or rigid polymer stop member is positioned in alignment with a sealable advancement mechanism for subsequent extension therethrough. A perforation separates the urine bag cavities from each other which is used for an aseptic presentation of the catheter advancement mechanism and the catheter.

One significant aspect and feature of the present invention is a disposable urine bag having a self-stored and contained extendable catheter with an advancing mechanism for a non-contact, easy to use device, having a lubricant reservoir within the advancement mechanism. The advancement mechanism for the urine bag includes a seal which mates with an extendable catheter.

Another significant aspect and feature of the present invention is a perforated tear seam between upper and lower flexible top and bottom bag members forming the cavities.

Still another significant aspect and feature of the present invention is the use of a highly absorbent chemical which combines with the urine or fluid to form a non-leaking, semi-solid mass within the disposable urine bag. While the specification is directed towards urine, the teachings of the present invention can be extended to any type of fluid.

Having thus described embodiments of the present invention, it is one object of the present invention to provide a single-unit disposable urine bag having a self-contained catheter with an advancing mechanism, chemical absorbent, and cavity drain.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
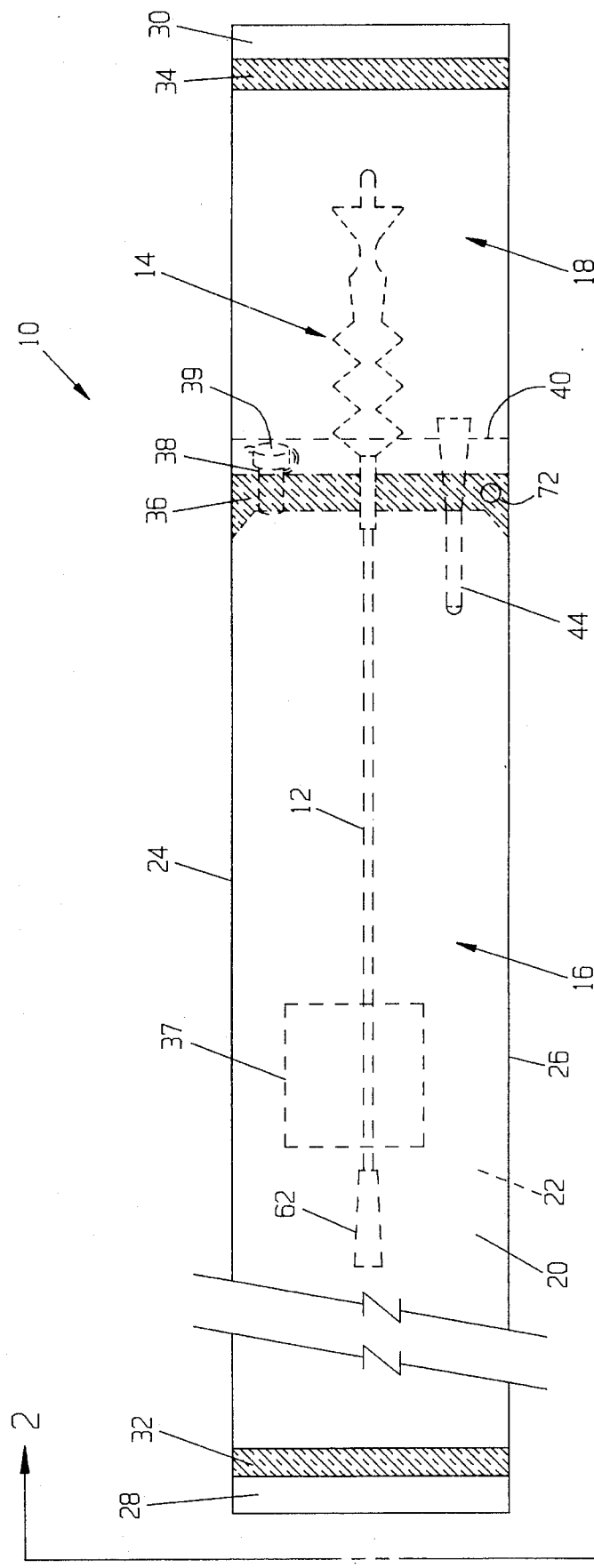
FIG. 1 illustrates a top view of the urine bag having a self-contained catheter and catheter advancement mechanism.

FIG. 1 illustrates a top view of a urine bag 10, the present invention, including a self-contained catheter 12 and a catheter advancement mechanism 14 in the urine bag 10. The urine bag 10 is of one-piece, and separable, polymer construction having a left cavity 16 for holding urine and a detachable adjacent right cavity 18 by a tearable perforation or like seam 40 for providing an aseptic cavity for enclosing medical structures as later described in detail. The closed cavity provides for protection against skin flora, handling and provides for an aseptic environment. The urine bag 10 is of a continuous construction and includes an essentially planar top flexible polymer member 20 and an opposing essentially planar bottom flexible polymer member 22 between edges 24 and 26. Ends 28 and 30 are suitably sealed by seals 32 and 34, such as by ultrasonic welding, gluing or other suitable processes known in the art, and are shown as being hatched to define such sealed areas. Edges 24 and 26 can also be secured, such as by welding or ultrasonic sealing or other like securing processes. Another configured welded or glued seal 36, which is also cross hatched, serves to form a barrier between the left and right cavities 16 and 18 and also to anchor the catheter advancement mechanism 14 to the left cavity 16. Cavity 18 is to facilitate the presentation of the catheter in an aseptic manner. The left cavity 16 is bounded by the top flexible polymer member 20, the bottom flexible polymer member 22, end seal 32 and seal 36. The right cavity 18 is bounded by the top flexible polymer member 20, the bottom flexible polymer member 22, the end seal 34 and the seal 36. The left cavity 16 stores the catheter 12 prior to use and is a collector and reservoir for urine. Also, a highly absorbent chemical 37, such as potassium or sodium polyacrylate, can be provided within the left cavity 16. Alternatively, a cavity drain 38 having an attached sealing cap 39 can also be included. The cavity drain 38 drains the left cavity 16, and is secured thereto by the weldment seal 36. The highly absorbent chemical 37, which can be in a pouch which dissolves with contact to water, urine or other fluid, and in granular form or other suitable form, is placed within the compartment 16. Urine or other aqueous medium is absorbed by the absorbent chemical medium 37, which expands to form a semi-solidified, gel-like material which has a putty-like consistency, thus eliminating any potential cavity leakage problems should a subsequent event such as a cavity puncture occur, or also for sanitary disposal.

The right cavity 18 houses one end of the catheter advancement mechanism 14 and includes a perforated tearable seam or a tearable seam 40, which allows the right cavity 18 to be separated from the left cavity member 16, thus exposing the distal end of the catheter advancement mechanism 14 just prior to deployment of the catheter 12 from the left cavity 16 as later described in detail. Also included is a leak-resistant small holster cavity 44 into which the distal end of the catheter 12 secures to preclude leakage of urine from the catheter 12 and left cavity 16 after urine bag usage. The holster cavity 44 secures to the left cavity 16 under the weldment seal 36. The catheter 12 includes a conical connector 62. A support hole 72 provides for securing of the urine bag to a stand or clothing of the user.

Figure 2:
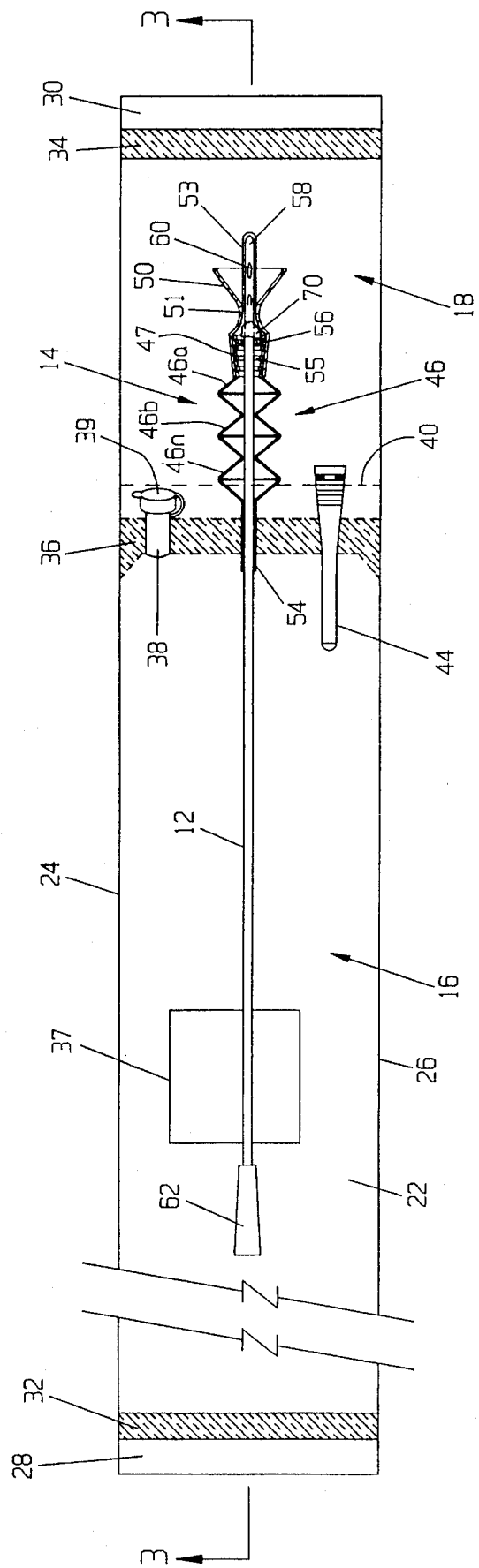
FIG. 2 illustrates a top view in horizontal cross section of the urine bag along line 2—2 of FIG. 1.

FIG. 2 illustrates a top view in horizontal cross section of the urine bag 10 generally along line 2—2 of FIG. 1 where all numerals correspond to those elements previously described. The top flexible member 20 has been removed for purpose of brevity and clarity of illustration. Weldment areas 32, 34 and 36 are illustrated in cross hatching for purposes of brevity and clarity. Illustrated in particular is the engagement of the catheter 12 with the catheter advancement mechanism 14. The two-section, soft polymer catheter advancement mechanism 14 includes, but is not limited to, a first flexible polymer portion having a soft pliable plastic conically shaped glands positioner 50, a narrow manipulation point 51, a tapered coupling 47, and an introducer 53 extending to the right of the glands positioner 50. The second flexible polymer portion includes a tapered and ringed coupler 55, a plurality of bellows members 46a–46n and a tubular member/manipulation point 54, which is anchored to the top and bottom flexible polymer members 20 and 22 by weldment seal 36. This bellows structure can be injection molded, blow molded or dipped polymer material. The tapered coupling 47 secures by suitable bonding and frictional engagement over and about the tapered and ringed coupler 55 to form the joined flexible portions of the catheter advancement mechanism 14. The catheter 12 includes a distal tip 58, one or more ports 60 in the distal tip 58, and a conical connector 62 at its proximal end, which acts as a stop against the tubular member/manipulation point 54 to preclude removal of the catheter completely from the confines of the left cavity 16 during deployment of the catheter advancement mechanism 14. The catheter 12 slidingly aligns through the tubular member/manipulation point 54, through the center of the bellows members 46a–46n, through the tapered and ringed coupler 55, through the manipulation point 51, through the glands positioner 50 and through the introducer 53 which has a double slotted end through which the distal end of the catheter 12 passes during deployment. The catheter 12 also passes through a U-cup seal 56 and lubricant 70 which are illustrated in the following figures. The catheter 12 is appropriately dimensioned to allow unrestricted passage and wiping of excessive lubricant by lumen 63 formed by the interior of the catheter advancement mechanism 14 illustrated in FIG. 4.

Figure 3:
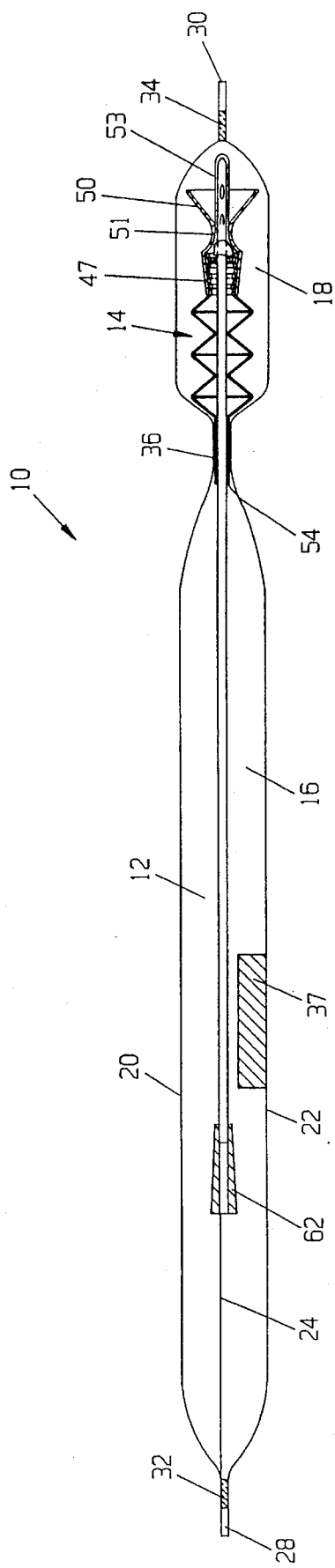
FIG. 3 illustrates a side view in cross section of the urine bag along line 3—3 of FIG. 2.

FIG. 3 illustrates a side view in cross section along line 3—3 of FIG. 2 of the urine bag 10 where all numerals correspond to those elements previously described. Illustrated in particular are the cavities 16 and 18 and the previously described components therein.

Figure 4:
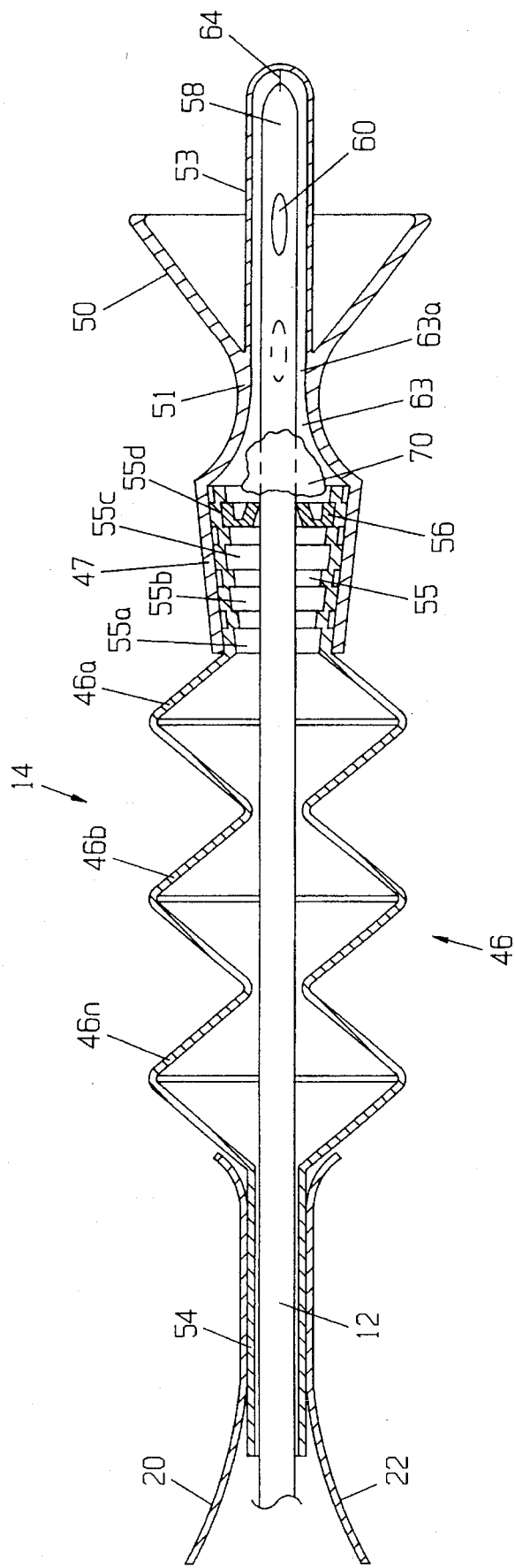
FIG. 4 illustrates a cross-sectional view of the catheter advancement mechanism prior to catheter advancement.

FIG. 4 illustrates a cross-sectional view of the catheter advancement mechanism 14 subsequent to removal of the right cavity 18 along the tear line 40 of FIG. 2 and ready for deployment of the catheter 12 where all numerals correspond to those elements previously described. The bellows 46 include bellow members 46a, 46b, and 46n, which can be a blow molded polymer. The tapered and ringed coupler 55 includes internal annular grooves 55a–55d any of which can provide for suitable nesting of a pliable U-cup seal 56, which can be of a suitable size to match the diameter of the catheter 12. Lubricant 70 is contained in a lumen 63 of the manipulation point 51 between the U-cup seal 56 and the ever narrowing lumen 63. The narrowest point 63a of the lumen 63 allows an appropriate amount of lubricant 70 to be applied to the advancing catheter 12. The tip of the introducer 53 includes two crossed slits forming an "x" to allow egress of the proximal end of the catheter 12 during deployment through the two expanded crossed slits which then separate and move outwardly.

MODE OF OPERATION

Figure 5:
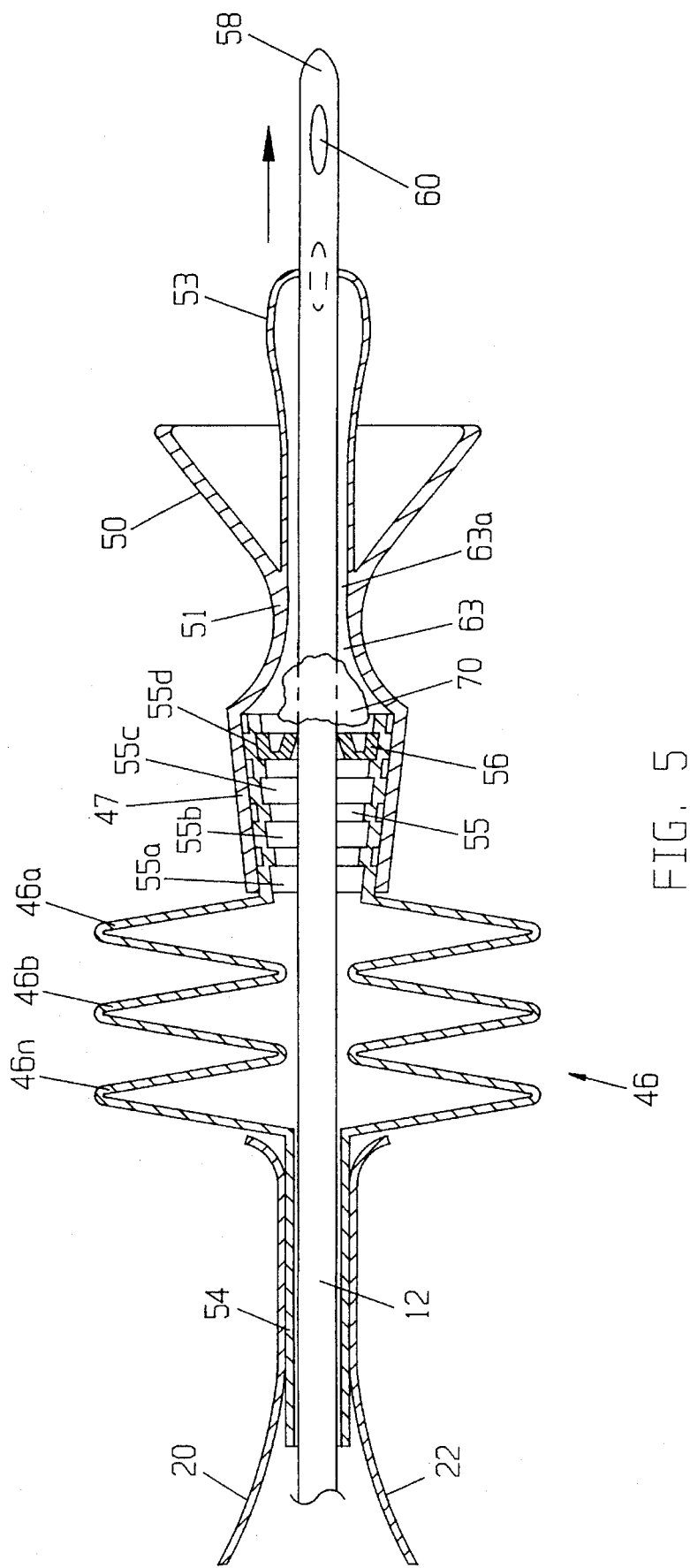
FIG. 5 illustrates the first advancement of the catheter and compression of the bellows mechanism subsequent to removal of the right cavity half; and, FIG. 6 illustrates the bellows in the relaxed mode subsequent to a number of catheter advancements by manipulation of the catheter advancement mechanism.
Figure 6:
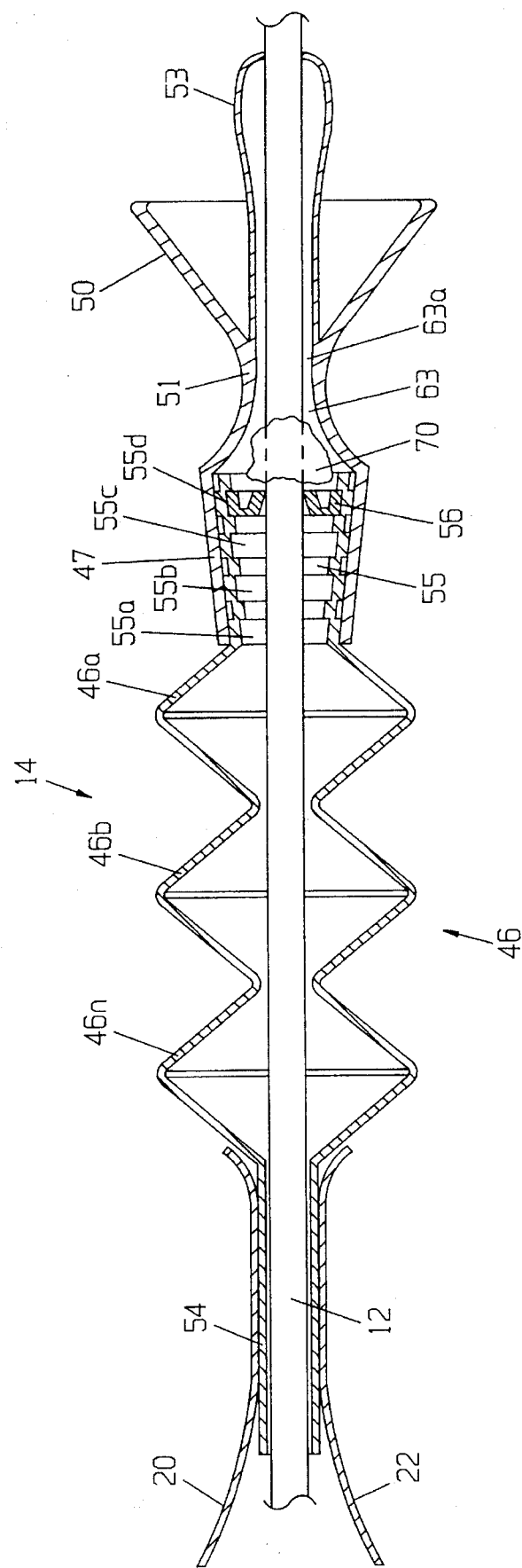

FIGS. 5–6 best illustrate the mode of operation including the advancement of the catheter 12 through the urine bag 10.

FIG. 5 illustrates the first advancement of the catheter 12 and compression of the bellows 46 where all numerals correspond to those elements previously described. The first advancement of the catheter 12 and compression of the bellows 46 is accomplished by manually compressing the flexible tubular member/manipulation point 54 against the catheter 12 and applying a forward force to the right, while with the other hand the glands positioner 50 is held against the gland. The introducer 53 is inserted into the meatus urethra and the catheter 12 is advanced to open and pass through the "x" slits in the end of the introducer 53.

Continued forward force is applied to insure that the catheter 12 enters the meatus urethra. If the catheter 12 has penetrated, the flexible manipulation point 51 is squeezed with the same hand to maintain the position of catheter 12 in the meatus urethra, and pressure is manually released at the flexible tubular member/manipulation point 54. This lets bellows section 46 spring back to the position shown in FIG. 6. This sequence is repeated until full insertion of the catheter 12 is complete. As this is accomplished, the flexible tubular member/manipulation point 54 and the glands positioner 50 are also relatively re-positioned proximally with respect to the catheter 12, having previously exposed the distal tip 58 of the catheter 12.

FIG. 6 illustrates the bellows 46 in the relaxed mode subsequent to a second and required number of additional advancements of the catheter 12 through the catheter advancement mechanism 14 until the catheter 12 has advanced sufficiently through the meatus urethra for required urine drainage. Removal of the catheter 12 is accomplished by grasping and applying pressure at the manipulation point 51 and then withdrawing the catheter 12 from the meatus urethra. The distal tip 58 is then secured within the holster cavity 44, thereby sealing the catheter 12 from inadvertent spillage. The interior of the holster cavity 44 is tapered to appropriately accommodate various diameter catheters.

Various modifications can be made to the present invention without departing from the apparent scope hereof.

We claim:

1. A urine bag comprising:
   a. two opposing polymer members forming a holding cavity means for urine and a clean cavity means for a catheter insertion means, and a seam means between said holding cavity means and said clean cavity means;
   b. said catheter insertion means including and connected in order a bellows means connected to one end of said holding cavity means and including a glands positioner;
   c. a catheter extending through said bellows means including a conical connector at one end for engaging with a tubular member in the end of said holding cavity means; and,
   d. a catheter holster means to captivate and seal said catheter and urine storage means upon completion of a voiding cycle.

2. The urine bag of claim 1 including an absorbing means in said holding cavity means.

3. The urine bag of claim 1 wherein said holding cavity means includes a cavity drain means.

4. The urine bag of claim 1 wherein said holding cavity means includes a leak-resistant holster cavity means.

5. The urine bag of claim 1 wherein said holding cavity means includes a support hole means.

6. The urine bag of claim 1 including a tubular member and manipulation point means in the end of said holding cavity means.

7. The urine bag of claim 1 wherein said seam means is a tearable seam.

8. The urine bag of claim 1 wherein said seam means is a perforated tearable seam means.

9. The urine bag of claim 1 including a lubricant in said bellows means.

10. A urine bag comprising:
    a. two opposing polymer members forming a holding cavity means for urine and a cavity means for a catheter insertion means, and a perforation means between said cavity means;
    b. said catheter insertion means including and connected in order, a bellows connected to one end of said holding cavity means, a tapered and ring coupler, a manipulation point, an introducer with crossed x slits, and a glands positioner at one end of said bellows means; and,
    c. a catheter including holes, extending through said catheter insertion means and including a conical connector at one end for engaging with a tubular member.

11. The urine bag of claim 10 including a urine or fluid absorption material in said holding cavity means.

12. The urine bag of claim 10 wherein said holding cavity means includes a cavity drain means.

13. The urine bag of claim 10 wherein said holding cavity means includes a holster cavity means.

14. The urine bag of claim 10 wherein said holding cavity means includes a support hole means.

15. The urine bag of claim 10 including a tubular member and manipulation point means in the end of said holding cavity means.

16. The urine bag of claim 10 wherein said seam means is tearable seam.

17. The urine bag of claim 10 wherein said seam means is a perforated tearable seam means.

18. The urine bag of claim 10 including a lubricant on said bellow means.

19. The urine bag of claim 10 including a fluid absorption material in a disposable package in said holding cavity means.

20. The urine bag of claim 10 including a hydrogel in said holding cavity means.

21. A urine bag comprising:
    a. two opposing polymer members forming a holding cavity means for urine and a cavity means for a catheter insertion means, and a perforation means between said cavity means;
    b. said catheter insertion means including and connected in order, a bellows means connected to one end of said holding cavity means, a tapered and ring coupler including internal annular grooves, a manipulation point, an introducer with crossed slits, and a glands positioner at one end of said bellows means; and,
    c. a catheter including holes extending through said catheter insertion means and including a conical connector at one end for engaging with a tubular member.

22. The urine bag of claim 21 including a urine or fluid absorption material in said holding cavity means.

23. The urine bag of claim 21 including a urine or fluid absorption material in a dissolvable package in said holding cavity means.

24. The urine bag of claim 21 wherein said holding cavity means includes a cavity drain means.

25. The urine bag of claim 21 wherein said holding cavity means includes a leak-resistant holster cavity means.

26. The urine bag of claim 21 wherein said holding cavity means includes a support hole means.

27. The urine bag of claim 21 including a tubular member and manipulation point means in the end of said holding cavity means.

28. The urine bag of claim 21 wherein said seam means is tearable seam.

29. The urine bag of claim 21 wherein said seam means is a perforated tearable seam means.

30. The urine bag of claim 21 including a lubricant in said catheter insertion means.

31. The urine bag of claim 21 wherein said bellow means is blow molded.

* * * * *